(12) United States Patent
Wang et al.

(10) Patent No.: US 8,419,679 B2
(45) Date of Patent: Apr. 16, 2013

(54) EMBOLIC PROTECTION SYSTEMS FOR BIFURCATED CONDUITS

(75) Inventors: Lixiao Wang, Long Lake, MN (US); Martin Chambers, Stillwater, MN (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/413,996

(22) Filed: Mar. 7, 2012

(65) Prior Publication Data

US 2012/0172967 A1  Jul. 5, 2012

Related U.S. Application Data

(63) Continuation of application No. 11/645,142, filed on Dec. 22, 2006, now Pat. No. 8,172,792.

(60) Provisional application No. 60/754,082, filed on Dec. 27, 2005.

(51) Int. Cl.
*A61M 29/00* (2006.01)

(52) U.S. Cl.
USPC .................................... 604/101.03

(58) Field of Classification Search ............... 604/101.03
See application file for complete search history.

(56) References Cited

U.S. PATENT DOCUMENTS

| | | | |
|---|---|---|---|
| 4,610,662 A | 9/1986 | Weikl et al. | |
| 4,636,195 A | 1/1987 | Wolinsky | |
| 4,795,427 A | 1/1989 | Helzel | |
| 4,824,436 A | 4/1989 | Wolinsky | |
| 5,135,484 A | 8/1992 | Wright | |
| 5,163,906 A | 11/1992 | Ahmadi | |
| 5,328,470 A | 7/1994 | Nabel et al. | |
| 5,380,284 A | 1/1995 | Don Michael | |
| 5,397,307 A | 3/1995 | Goodin | |
| 5,558,642 A | 9/1996 | Schweich, Jr. et al. | |
| 5,599,307 A | 2/1997 | Bacher et al. | |
| 5,613,948 A | 3/1997 | Avellanet | |
| 5,662,609 A | 9/1997 | Slepian | |
| 5,772,632 A | 6/1998 | Forman | |
| 5,833,650 A | 11/1998 | Imran | |
| 5,908,407 A | 6/1999 | Frazee et al. | |
| 5,911,725 A | 6/1999 | Boury | |
| 5,947,985 A | 9/1999 | Imran | |
| 6,126,635 A | 10/2000 | Simpson et al. | |
| 6,165,199 A * | 12/2000 | Barbut | 606/200 |
| 6,290,729 B1 | 9/2001 | Slepian et al. | |
| 6,312,444 B1 | 11/2001 | Barbut | |
| 6,387,119 B2 | 5/2002 | Wolf et al. | |
| 6,443,941 B1 | 9/2002 | Slepian et al. | |
| 6,454,741 B1 * | 9/2002 | Muni et al. | 604/96.01 |

(Continued)

*Primary Examiner* — Nicholas Lucchesi
*Assistant Examiner* — Diva K Chander
(74) *Attorney, Agent, or Firm* — Alana T. Bergman, Esq.

(57) ABSTRACT

An apparatus for removing emboli from a vessel during an interventional procedure comprising a catheter. The catheter includes: an elongate member having a lumen extending from the proximal end to the distal end; a dilation element disposed on a distal portion of the elongate member, the dilation element having a contracted state and an expanded state; an occlusion element disposed on a distal portion of the elongate member, the occlusion element being disposed proximal of the dilation element, and the occlusion element having a contracted state and an expanded state; and one or more aspiration ports disposed on a distal portion of the elongate member, the one or more aspiration ports being in fluid communication with the lumen, and one or more of the aspiration ports being disposed proximal of the dilation element and distal of the occlusion element.

28 Claims, 12 Drawing Sheets

U.S. PATENT DOCUMENTS

| | | |
|---|---|---|
| 6,485,500 B1 | 11/2002 | Kokish et al. |
| 6,527,739 B1 * | 3/2003 | Bigus et al. ............... 604/101.01 |
| 6,533,800 B1 | 3/2003 | Barbut |
| 6,569,146 B1 | 5/2003 | Werner et al. |
| 6,595,953 B1 | 7/2003 | Coppi et al. |
| 6,620,148 B1 | 9/2003 | Tsugita |
| 6,673,040 B1 * | 1/2004 | Samson et al. ............ 604/101.01 |
| 6,682,505 B2 | 1/2004 | Bates et al. |
| 6,689,097 B2 | 2/2004 | Thramann |
| 6,716,237 B1 * | 4/2004 | Alt ................................ 623/1.11 |
| 6,730,063 B2 * | 5/2004 | Delaney et al. ............... 604/173 |
| 6,740,107 B2 | 5/2004 | Loeb et al. |
| 6,743,196 B2 * | 6/2004 | Barbut et al. ............. 604/101.01 |
| 6,790,196 B2 | 9/2004 | Kokate et al. |
| 6,840,949 B2 | 1/2005 | Barbut |
| 6,887,227 B1 | 5/2005 | Barbut |
| 6,905,490 B2 | 6/2005 | Parodi |
| 6,929,633 B2 | 8/2005 | Evans et al. |
| 6,936,057 B1 | 8/2005 | Nobles |
| 6,972,030 B2 * | 12/2005 | Lee et al. ...................... 623/1.11 |
| 6,997,898 B2 | 2/2006 | Forman |
| 7,060,051 B2 * | 6/2006 | Palasis .................... 604/101.01 |
| 7,083,594 B2 | 8/2006 | Coppi |
| 7,252,650 B1 | 8/2007 | Andrews et al. |
| 7,300,459 B2 | 11/2007 | Heuser |
| 7,329,237 B2 | 2/2008 | Yokoyama et al. |
| 7,572,272 B2 | 8/2009 | Denison et al. |
| 7,740,609 B2 * | 6/2010 | Rowe et al. .............. 604/101.05 |
| 7,763,010 B2 * | 7/2010 | Evans et al. ................... 604/508 |
| 7,771,448 B2 * | 8/2010 | Ravikumar ................... 606/194 |
| 2001/0047184 A1 | 11/2001 | Connors, III |
| 2002/0010418 A1 | 1/2002 | Lary et al. |
| 2002/0016565 A1 | 2/2002 | Zadno-Azizi et al. |
| 2002/0107479 A1 * | 8/2002 | Bates et al. ................. 604/96.01 |
| 2002/0165574 A1 | 11/2002 | Ressemann et al. |
| 2002/0169436 A1 | 11/2002 | Gurm et al. |
| 2002/0169458 A1 | 11/2002 | Connors, III |
| 2003/0187495 A1 | 10/2003 | Cully et al. |
| 2004/0006306 A1 * | 1/2004 | Evans et al. .............. 604/101.03 |
| 2004/0006370 A1 * | 1/2004 | Tsugita ........................ 606/200 |
| 2004/0024448 A1 | 2/2004 | Chang et al. |
| 2004/0220521 A1 * | 11/2004 | Barbut ....................... 604/96.01 |
| 2005/0033334 A1 | 2/2005 | Santra et al. |
| 2005/0085770 A1 | 4/2005 | Don Michael |
| 2005/0090846 A1 | 4/2005 | Pedersen et al. |
| 2005/0154443 A1 | 7/2005 | Linder et al. |
| 2005/0177186 A1 | 8/2005 | Cully et al. |
| 2005/0181004 A1 * | 8/2005 | Hunter et al. .................. 424/422 |
| 2005/0192620 A1 | 9/2005 | Cully et al. |
| 2005/0273051 A1 | 12/2005 | Coppi |
| 2006/0095066 A1 | 5/2006 | Chang et al. |
| 2006/0149350 A1 | 7/2006 | Patel et al. |
| 2006/0253186 A1 | 11/2006 | Bates |
| 2006/0259066 A1 | 11/2006 | Euteneuer |
| 2006/0265082 A1 | 11/2006 | Meade et al. |
| 2007/0021774 A1 | 1/2007 | Hogendijk |
| 2007/0150044 A1 | 6/2007 | Wang et al. |
| 2007/0250105 A1 | 10/2007 | Ressemann et al. |

* cited by examiner

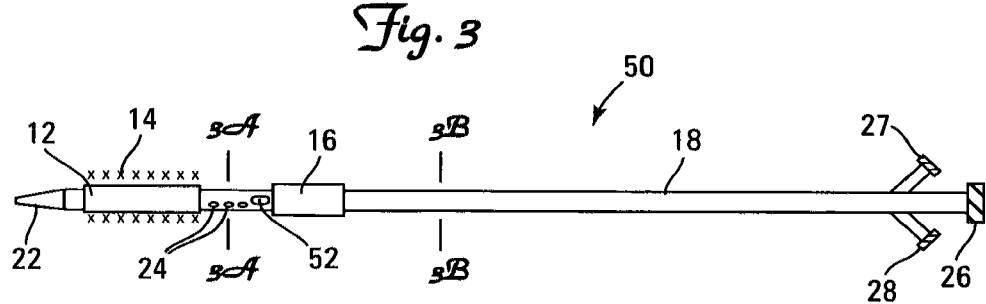
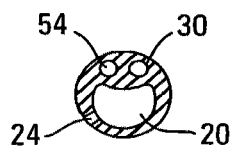 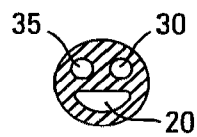
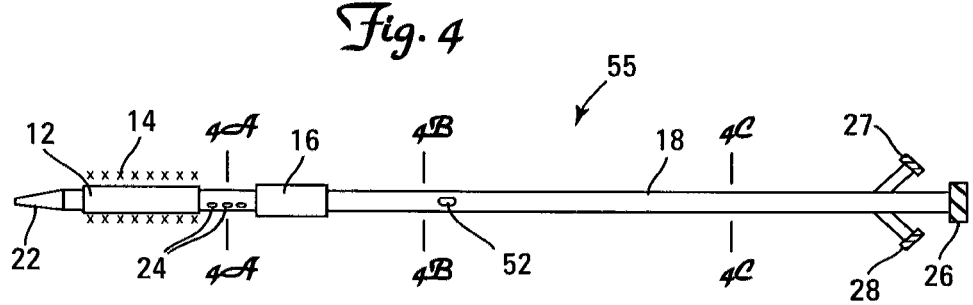
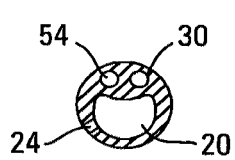 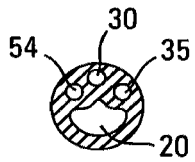 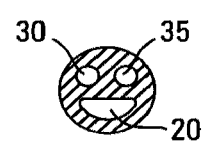

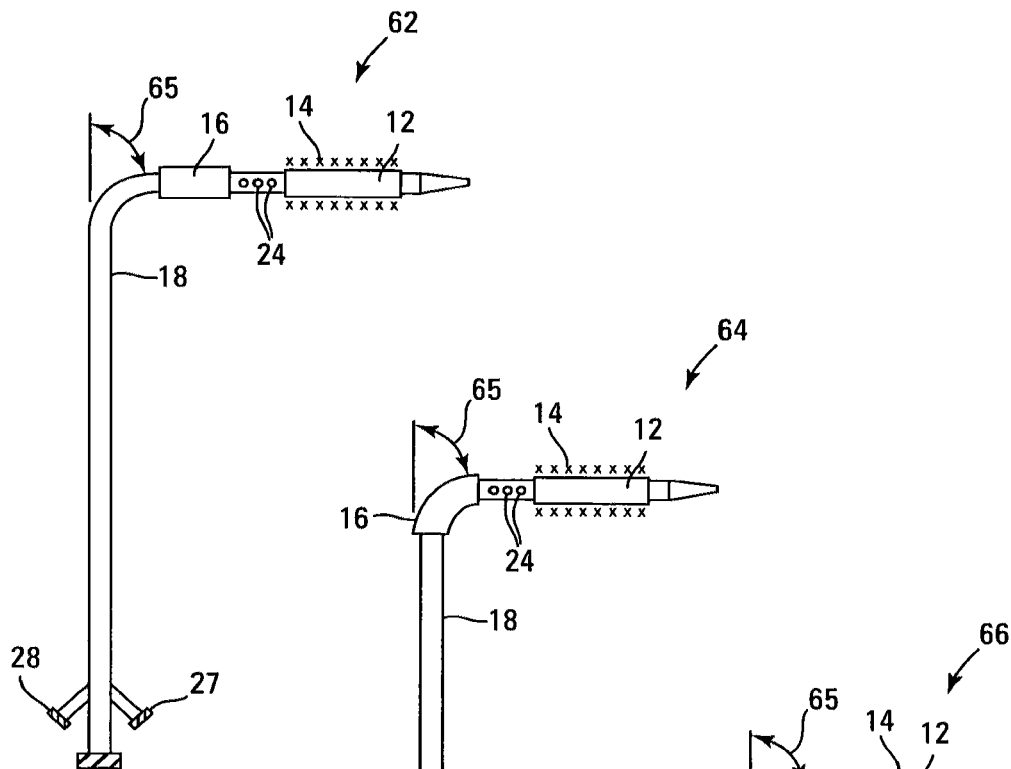
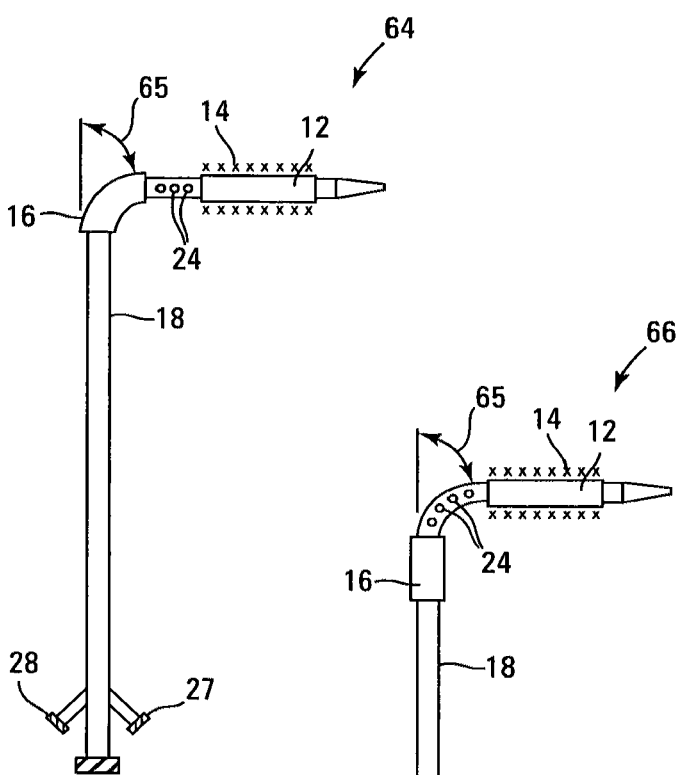
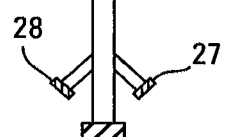
Fig. 6A
Fig. 6B
Fig. 6C

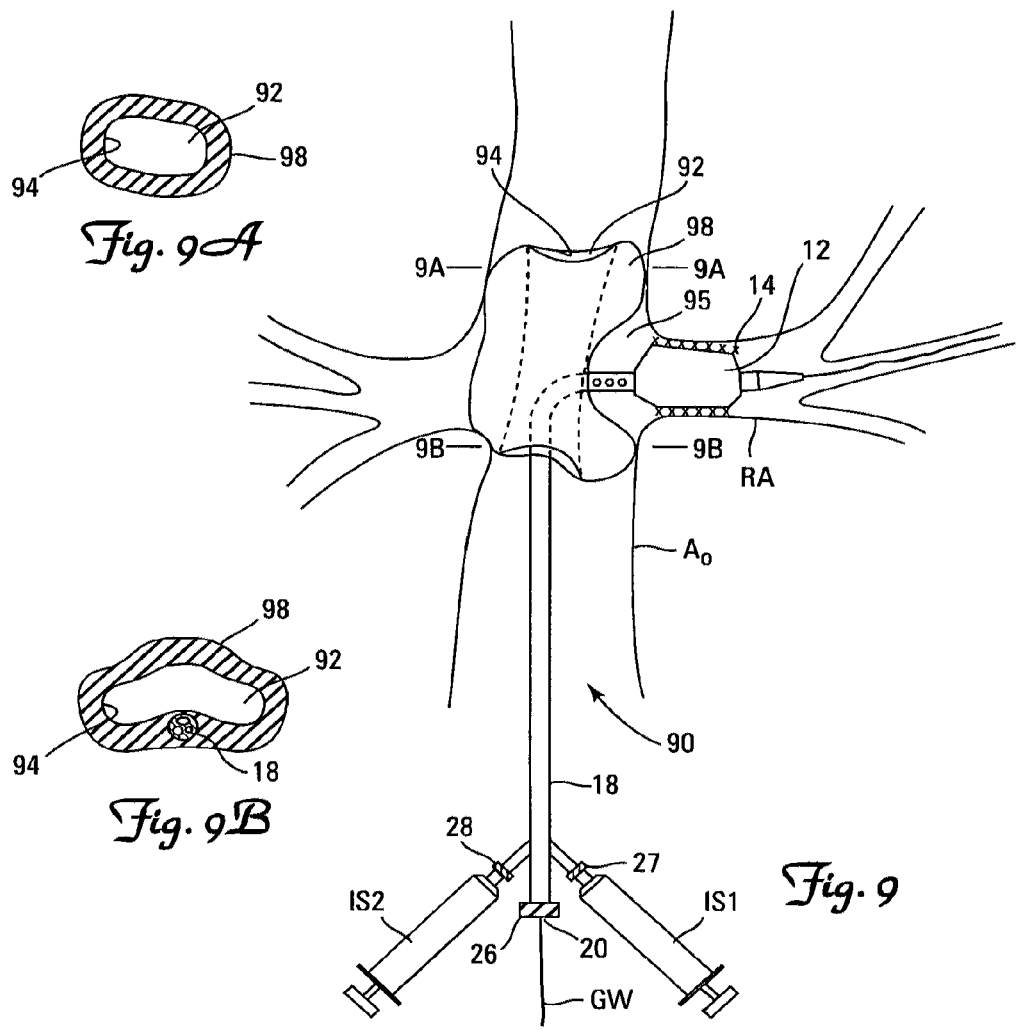

EMBOLIC PROTECTION SYSTEMS FOR BIFURCATED CONDUITS

This application is a continuation of U.S. application Ser. No. 11/645,142, filed Dec. 22, 2006, which claims the benefit of U.S. Provisional Application No. 60/754,082, filed Dec. 27, 2005, entitled "Embolic Protection System for Bifurcated Conduits," the contents of each of which are hereby incorporated by reference herein.

FIELD OF THE INVENTION

The present invention relates to embolic protection systems, and, more particularly, to embolic protection systems for ostial locations in blood vessels.

BACKGROUND OF THE INVENTION

Vessels are commonly treated to reduce or eliminate narrowings caused by arteriosclerotic disease. Interventional treatments can include use of balloon angioplasty, stenting, thrombectomy, atherectomy, and other procedures. During treatment particulate debris can be generated at the treatment site. Infarcts, strokes, and other major or minor adverse events are caused when debris embolizes into vasculature distal to the treatment site.

To prevent embolization of debris, embolic protection devices have been developed. During a procedure such devices can be placed distal or proximal to the treatment site. Embolic protection devices can remove emboli from the bloodstream by filtering debris from blood, by occluding blood flow followed by aspiration of debris, or can cause blood flow reversal to effect removal of debris. The shape, length and other characteristics of an embolic protection device are typically chosen based on the anatomical characteristics in the vicinity of the treatment site. However, some treatment sites present specific challenges due to anatomical shape or configuration. Known embolic protection devices are generally unsuitable for protection of vessels downstream of lesions at or near bifurcations because it is hard to protect both distal branches. Another challenging situation involves treatment of arteriosclerotic disease at the ostium of renal arteries within the human body. Known embolic protection devices are generally unsuitable for protection of vessels downstream of lesions at or near the main renal artery because the artery is short and divides downstream into three or more branch vessels.

Accordingly, a need exists for an embolic protection device that will prevent embolization of debris generated at treatment sites upstream from vessel branch sites.

SUMMARY OF THE INVENTION

According to one aspect of the present invention, an embolic protection device comprises a balloon expandable segment which is deployed in a renal artery, a balloon expandable segment which is deployed in the aorta, and an aspiration lumen. The balloon expandable segment deployed in the renal artery may have a stent mounted thereon. The balloon expandable segment deployed in the renal vessel treats disease in the renal vessel. The balloon expandable segment in the aorta expands to conform to the aortic region of the vessel, preventing blood flow into the renal vessel during treatment. The aspiration lumen removes debris from the vicinity of the treatment site.

The invention provides an apparatus for removing emboli from a vessel during an interventional procedure comprising a catheter, the catheter comprising: an elongate member configured to be advanced along a vascular path of a patient, the elongate member having a proximal portion, a distal portion, a proximal end, a distal end, and a lumen extending from the proximal end to the distal end; a dilation element disposed on a distal portion of the elongate member, the dilation element having a contracted state and an expanded state; an occlusion element disposed on a distal portion of the elongate member, the occlusion element being disposed proximal of the dilation element, and the occlusion element having a contracted state and an expanded state; and one or more aspiration ports disposed on a distal portion of the elongate member, the one or more aspiration ports being in fluid communication with the lumen, and one or more of the aspiration ports being disposed proximal of the dilation element and distal of the occlusion element. In one embodiment, the dilation element comprises a balloon. In another embodiment, the occlusion element comprises a balloon.

The invention provides an apparatus for removing emboli from a vessel during an interventional procedure comprising a catheter, a stent, and a sheath, the catheter comprising: an elongate member configured to be advanced along a vascular path of a patient, the elongate member having a proximal portion, a distal portion, a proximal end, a distal end, and a lumen extending from the proximal end to the distal end; an occlusion element disposed on a distal portion of the elongate member, the occlusion element having a contracted state and an expanded state; one or more aspiration ports disposed on a distal portion of the elongate member, and one or more of the aspiration ports being disposed proximal of the dilation element and distal of the occlusion element; the stent being disposed on a distal portion of the elongate member, the stent being disposed distal of the occlusion element; and the sheath being disposed over the stent.

The invention provides a method for positioning an apparatus within a patient's blood vessel, the method comprising: providing an apparatus described herein; providing a guidewire having a proximal end and a distal end; advancing the guidewire to a target site within the patient's blood vessel; and advancing the catheter over the guide wire by inserting the guidewire through the lumen extending between the proximal and distal ends of the catheter.

It is to be understood that both the foregoing general description and the following detailed description are exemplary and explanatory and are intended to provide further explanation of the invention as claimed.

BRIEF DESCRIPTION OF THE DRAWINGS

The above and further advantages of the invention may be better understood by referring to the following description in conjunction with the accompanying drawings.

FIGS. 3, 3A and 3B illustrate conceptually a partial cross-sectional diagram of an alternative embodiment of an embolic protection and stent delivery system in accordance with the present invention.

FIGS. 4 and 4A to 4C illustrate conceptually a partial cross-sectional diagram of an alternative embodiment of an embolic protection and stent delivery system in accordance with the present invention.

FIGS. 6A to 6C illustrate conceptually a partial cross-sectional diagram of alternative embodiments of embolic protection and stent delivery systems in accordance with the present invention.

FIGS. 9, 9A and 9B illustrate conceptually a partial cross-sectional diagram of an alternative embodiment of an embolic protection and stent delivery system in accordance with the present invention.

DETAILED DESCRIPTION

Figure 1:
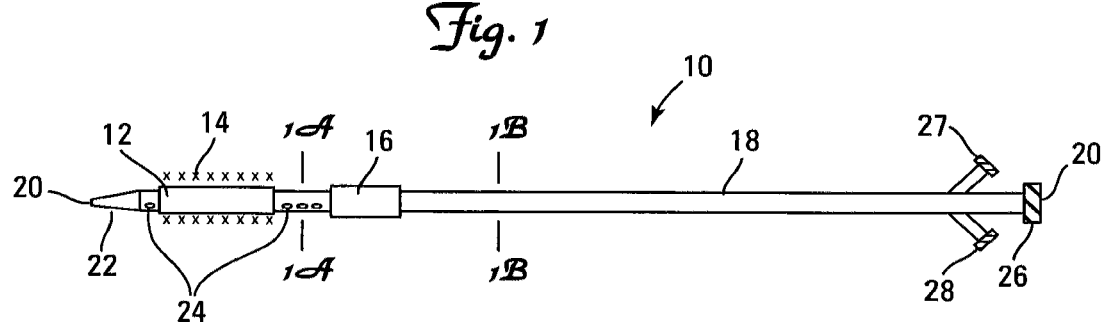
FIGS. 1, 1A and 1B illustrate conceptually a partial cross-sectional diagram of an embolic protection and stent delivery system in accordance with the present invention.
Figure 1A:
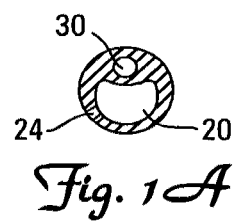
Figure 1B:
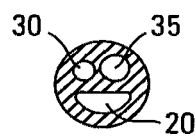

The terms "distal" and "proximal" as used herein refer to the relative position of the guidewire and catheters in a lumen. The most "proximal" point of the catheter is the end of the catheter extending outside the body closest to the physician. The most "distal" point of the catheter is the end of the catheter placed farthest into a body lumen from the entrance site.

The invention provides an apparatus for removing emboli from a vessel during an interventional procedure comprising a catheter, the catheter comprising: an elongate member configured to be advanced along a vascular path of a patient, the elongate member having a proximal portion, a distal portion, a proximal end, a distal end, and a lumen extending from the proximal end to the distal end; a dilation element disposed on a distal portion of the elongate member, the dilation element having a contracted state and an expanded state; an occlusion element disposed on a distal portion of the elongate member, the occlusion element being disposed proximal of the dilation element, and the occlusion element having a contracted state and an expanded state; and one or more aspiration ports disposed on a distal portion of the elongate member, the one or more aspiration ports being in fluid communication with the lumen, and one or more of the aspiration ports being disposed proximal of the dilation element and distal of the occlusion element. In one embodiment, the dilation element comprises a balloon. In another embodiment, the occlusion element comprises a balloon. In one embodiment, the elongate member comprises a sidewall around the lumen and one or more aspiration ports disposed proximal of the dilation element and distal of the occlusion element are holes through the sidewall.

In one embodiment, the dilation element is a stent-delivery element. In an embodiment, the stent-delivery element comprises a balloon. In one embodiment, the dilation element is an angioplasty balloon. In another embodiment, the catheter comprises an occlusion balloon hub on the proximal portion of the catheter and an occlusion balloon lumen connecting the occlusion balloon hub and the occlusion element. In one embodiment, the catheter comprises a dilation balloon hub on the proximal portion of the catheter and a dilation balloon lumen connecting the dilation balloon hub and the dilation element.

In one embodiment, the catheter comprises two or more aspiration ports disposed proximal of the dilation element and distal of the occlusion element. In one embodiment, the elongate member comprises a sidewall around the lumen and the two or more aspiration ports are holes through the sidewall.

In one embodiment, the catheter comprises a skive. In an embodiment, the skive is located on a distal portion of the elongate tubular body, proximal of the dilation element and distal of the occlusion element. In an embodiment, the skive is located on a distal portion of the elongate tubular member, proximal of the occlusion element.

In one embodiment, the catheter has a pre-set bend. The pre-set bend can be at an angle of from about 10 degrees to about 170 degrees, an angle of from about 45 degrees to about 135 degrees, an angle of from about 75 degrees to about 105 degrees, or at an angle of about 90 degrees. In embodiments of the invention, the pre-set bend is located proximal of the occlusion element, the pre-set bend is located at the occlusion element, or the pre-set bend is located distal of the occlusion element and proximal of the dilation element.

In one embodiment, the occlusion element comprises a perfusion lumen. In an embodiment, the occlusion element has a longitudinal axis and the perfusion lumen encompasses the longitudinal axis.

The invention provides an apparatus comprising the apparatus described herein and further comprising a guidewire. In an embodiment, the guidewire is sized to pass through the lumen of the catheter.

The invention provides an apparatus comprising the apparatus described herein and further comprising a stent. In an embodiment, the stent is disposed on the dilation element.

The invention provides an apparatus comprising the apparatus described herein and further comprising an adapter comprising a distal hub, sidearm hub, and hemostatic valve.

The invention provides an apparatus comprising the apparatus described herein and further comprising a sheath. In an embodiment, the sheath is disposed over a portion of the catheter.

The invention provides an apparatus for removing emboli from a vessel during an interventional procedure comprising a catheter, a stent, and a sheath, the catheter comprising: an elongate member configured to be advanced along a vascular path of a patient, the elongate member having a proximal portion, a distal portion, a proximal end, a distal end, and a lumen extending from the proximal end to the distal end; an occlusion element disposed on a distal portion of the elongate member, the occlusion element having a contracted state and an expanded state; and one or more aspiration ports disposed on a distal portion of the elongate member, and one or more of the aspiration ports being disposed proximal of the dilation element and distal of the occlusion element; the stent being disposed on a distal portion of the elongate member, the stent being disposed distal of the occlusion element; and the sheath being disposed over the stent.

The invention provides a method for positioning an apparatus within a patient's blood vessel, the method comprising: providing an apparatus described herein; providing a guidewire having a proximal end and a distal end; advancing the guidewire to a target site within the patient's blood vessel; and advancing the catheter over the guide wire by inserting the guidewire through the lumen extending between the proximal and distal ends of the catheter. In one embodiment, the dilation element is expanded, and then the occlusion element is expanded. In one embodiment, after the occlusion element has been expanded, blood is aspirated through the one or more aspiration ports disposed proximal of the dilation element and distal of the occlusion element. In one embodiment, the guidewire is removed before the blood is aspirated. In another embodiment, after the blood has been aspirated, the dilation element is contracted, and then the occlusion element is contracted.

In one embodiment, the distal portion of the catheter is positioned in a renal artery of the patient. In one embodiment, the occlusion element is positioned in the renal aorta and the dilation element is positioned in the renal artery.

FIG. 1 illustrates an embolic protection and stent delivery system 10 in accordance with the present invention. Embolic protection and stent delivery system 10 comprises a dilation balloon 12, expandable stent 14, occlusion balloon 16, and catheter shaft 18. Dilation balloon 12 may comprise nylon, polyester, polyolefin, or other materials commonly used in the art suitable for expansion of stents or vessels, and the balloon material, if polymeric, may be oriented. Expandable stent 14 may comprise stainless steel alloys, cobalt chrome alloys, titanium, tantalum, platinum, gold, or other materials or their alloys as are known in the art. Occlusion balloon 16 may comprise nylon, polyester, polyolefin, polyethylene, latex, silicone, polyurethane, or other materials commonly used in the art suitable for occlusion of vessels, and the balloon material may be oriented. Catheter shaft 18 may comprise polyether block amides (PEBAX®), polyethylene, nylon, polyester, HYTREL® polyester, polyimide, or other materials commonly used in the art suitable for interventional catheters.

Embolic protection and stent delivery system 10 further comprises lumen 20 which is continuous from tip 22 to aspiration hub 26. One or more aspiration holes 24 are provided through sidewall of catheter 18. Lumen 20 can be used for aspiration of emboli proximally through catheter 18. A guidewire (not shown) can be inserted into lumen 20 and catheter 18 tracked over the guidewire. Interior of dilation balloon 12 is in fluid communication with lumen 30 and lumen 30 is continuous from dilation balloon 12 to dilation balloon hub 27. Interior of occlusion balloon 16 is in fluid communication with lumen 35 and lumen 35 is continuous from occlusion balloon 16 to occlusion balloon hub 28. Expandable stent 14 is firmly mounted on dilation balloon 12 by crimping or using other means as are commonly known in the art.

Figure 2:
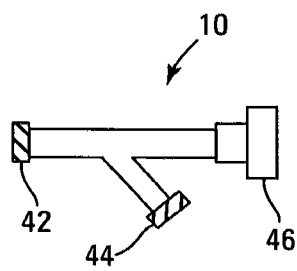
FIG. 2 illustrates conceptually a side view of an adapter used in accordance with the present invention.

FIG. 2 illustrates an adapter used in accordance with the present invention. Adapter 40 comprises distal hub 42, sidearm hub 44, and hemostasis valve 46. A lumen (not shown) is in fluid communication with distal hub 42, sidearm hub 44, and hemostasis valve 46.

FIGS. 3 and 4 illustrate alternative embodiments of an embolic protection and stent delivery system in accordance with the present invention. Embolic protection and stent delivery systems 50 and 55 comprise lumen 20 which is continuous from tip 22 to aspiration hub 26. One or more aspiration holes 24 are provided through sidewall of catheter 18. Lumen 20 can be used for aspiration of emboli proximally through catheter 18. Skive 52 is provided for use with a guidewire. Lumen 54 is continuous from tip 22 to skive 52. A guidewire (not shown) can be inserted into lumen 54, and catheter 18 tracked over the guidewire in a rapid exchange configuration. Interior of dilation balloon 12 is in fluid communication with lumen 30, and lumen 30 is continuous from dilation balloon 12 to dilation balloon hub 27. Interior of occlusion balloon 16 is in fluid communication with lumen 35, and lumen 35 is continuous from occlusion balloon 16 to occlusion balloon hub 28.

Figure 5:
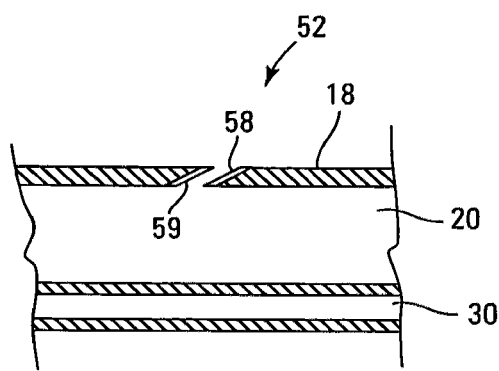
FIG. 5 illustrates conceptually a cross-sectional diagram of a wire skive in accordance with the present invention.

FIG. 5 illustrates a wire skive in accordance with the present invention. Skive 52 is provided for use with a guidewire and consists of a passageway formed into the wall of catheter 18. In some embodiments skive 52 is formed into the wall of catheter 18 at the most proximal end of lumen 54 (not shown). In a preferred embodiment skive 52 is formed into the wall of catheter 18 and fluidly communicates with lumen 20 at a location in the distal half of the length of catheter 18 (shown), thereby eliminating the need for a guidewire lumen separate from aspiration lumen 20. In some embodiments it is desirable to line the interior passage 59 of skive 52 with sealing material 58 so that there will be minimal loss of aspiration at skive 52 when aspirating through lumen 20. Sealing material 58 may comprise a soft or spongy polymer such as butyl rubber, EVA foam, latex foam, polyurethane foam, or other sealing materials as are known in the art.

FIGS. 6A to 6C illustrate alternative embodiments of embolic protection and stent delivery systems in accordance with the present invention. Embolic protection and stent delivery systems 62, 64 and 66 comprise catheter 18 with pre-set bend 65. Pre-set bend 65 may be a simple in-plane bend and comprise any angle from about 10 degrees to about 170 degrees, more preferably about 45 degrees to about 135 degrees, and more preferably about 75 degrees to about 105 degrees. In one embodiment, the pre-set bend is at an angle of about 90 degrees. Pre-set bend 65 is provided to simplify delivery of embolic protection and stent delivery systems 62, 64 and 66 to specific anatomies. See, for example, FIG. 6A, where pre-set bend 65 is a simple in-plane bend and comprises an angle of about 90 degrees. Pre-set bend may also comprise multiple spaced apart bends, compound bends, or out of plane bends as required by the anatomy in the vicinity of a treatment site. FIG. 6A illustrates embolic protection and stent delivery system 62 having pre-set bend 65 located proximal to occlusion balloon 16, FIG. 6B illustrates embolic protection and stent delivery system 64 having pre-set bend 65 located at occlusion balloon 16, and FIG. 6C illustrates embolic protection and stent delivery system 62 having pre-set bend 65 located distal to occlusion balloon 16 but proximal to dilation balloon 12. The exact location of pre-set bend 65 along catheter 18 will depend upon the anatomy in the vicinity of a treatment site.

Figure 7:
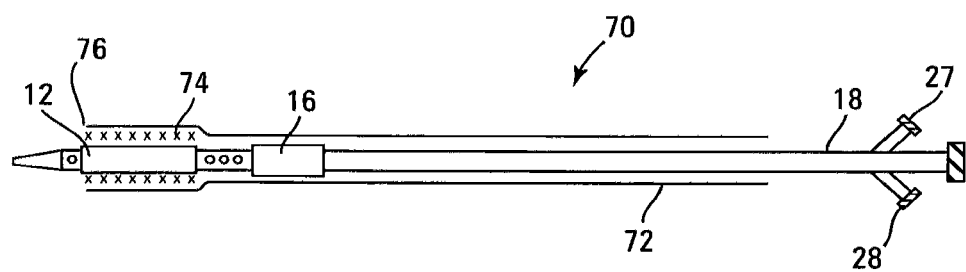
FIG. 7 illustrates conceptually a partial cross-sectional diagram of an alternative embodiment of an embolic protection and stent delivery system in accordance with the present invention.

FIG. 7 illustrates an alternative embodiment of an embolic protection and stent delivery system in accordance with the present invention. Embolic protection and stent delivery system 70 is similar to embolic protection and stent delivery system 10, except that system 70 comprises self-expanding stent 74 and sheath 72. Sheath 72 has distal end 76. Self expanding stent 74 may comprise high elastic limit materials such as ELGILOY® alloy, cobalt chrome alloys, or other materials as are known in the art. Self expanding stent 74 may comprise so-called shape-memory metals such as nitinol. Shape-memory metal stents can self-expand when thermo-mechanically processed to exhibit superelastic material properties. Such shape-memory stents can also self-expand through use of a pre-programmed shape memory effect. Stents processed to exhibit a shape memory effect experience a phase change at the elevated temperature of the human body. The phase change results in expansion of the stent from a collapsed state to an enlarged state. Sheath 74 may comprise polyester, polytetrafluoroethylene (PTFE), nylon, polyester block amides (PEBAX®), HYTREL® polyester, polyetheretherketone (PEEK), polyamide, and other materials as are commonly known in the art. Dilation balloon 12, lumen 30, dilation balloon hub 27 may be omitted from embolic protection and stent delivery system 70 if desired. In use sheath 72 is moved proximally relative to self-expanding stent 74 thereby allowing stent 74 to self-expand. In one embodiment dilation balloon 12 is inflated to post-dilate self-expanding stent 74.

Figure 8A:
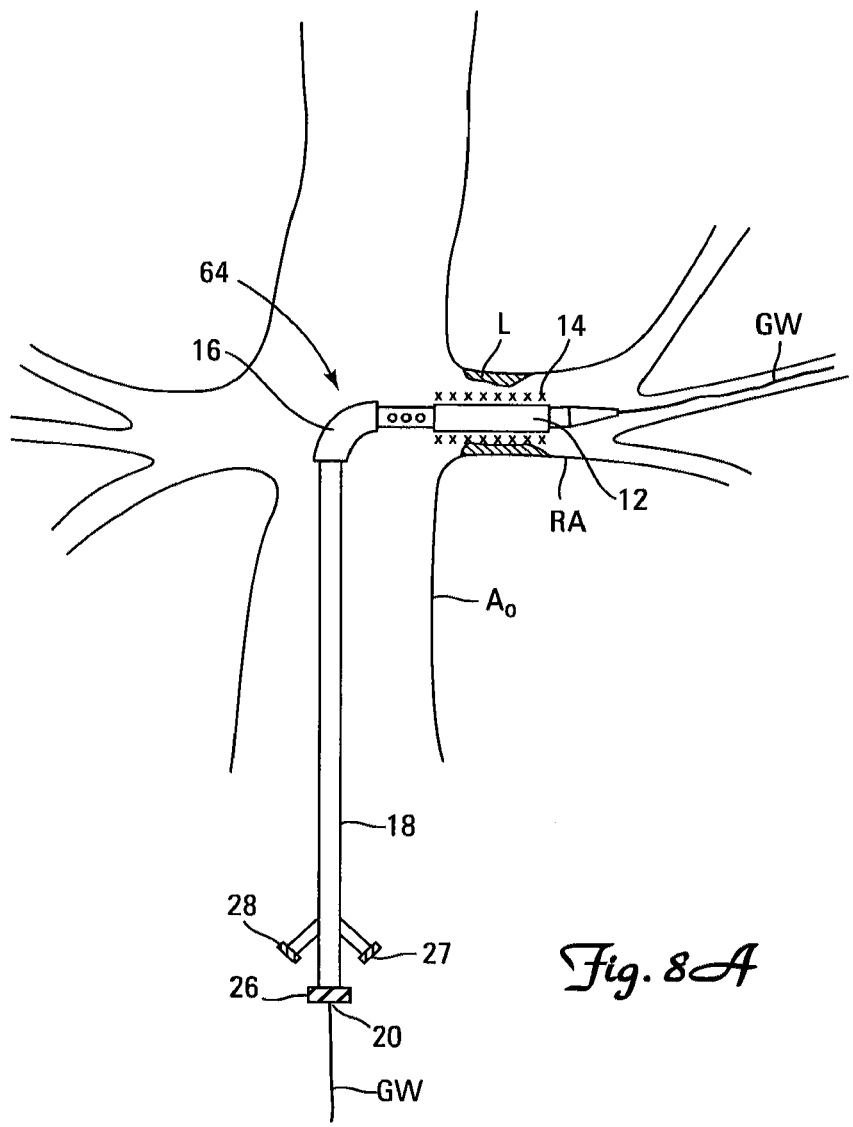
FIGS. 8A to 8F illustrate conceptually a method of using an embolic protection and stent delivery system in accordance with the present invention.

FIGS. 8A to 8F illustrate a method of using an embolic protection and stent delivery system in accordance with the present invention. Embolic protection and stent delivery system 64 is introduced into the arterial vasculature using conventional techniques, advanced over guidewire GW through aorta Ao and into renal artery RA as illustrated in FIG. 8A.

Figure 8B:
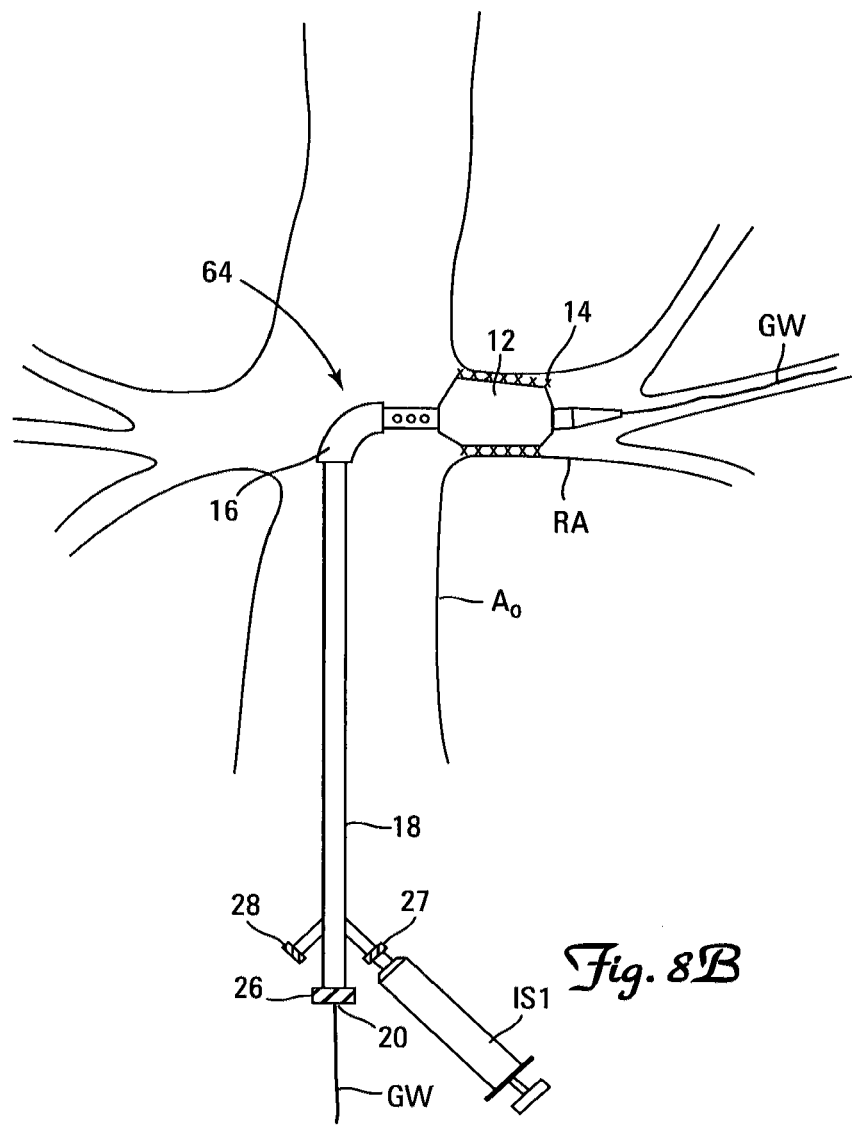

Position of catheter 18 is adjusted until stent 14 is located at desired treatment site such as at lesion L. Inflation source IS1, for example a syringe or a high pressure inflation device, is attached to dilation balloon hub 27 and dilation balloon 12 is inflated using inflation source IS1. Inflated dilation balloon 12 compresses lesion L and expands stent 14, as illustrated in FIG. 8B.

Figure 8C:
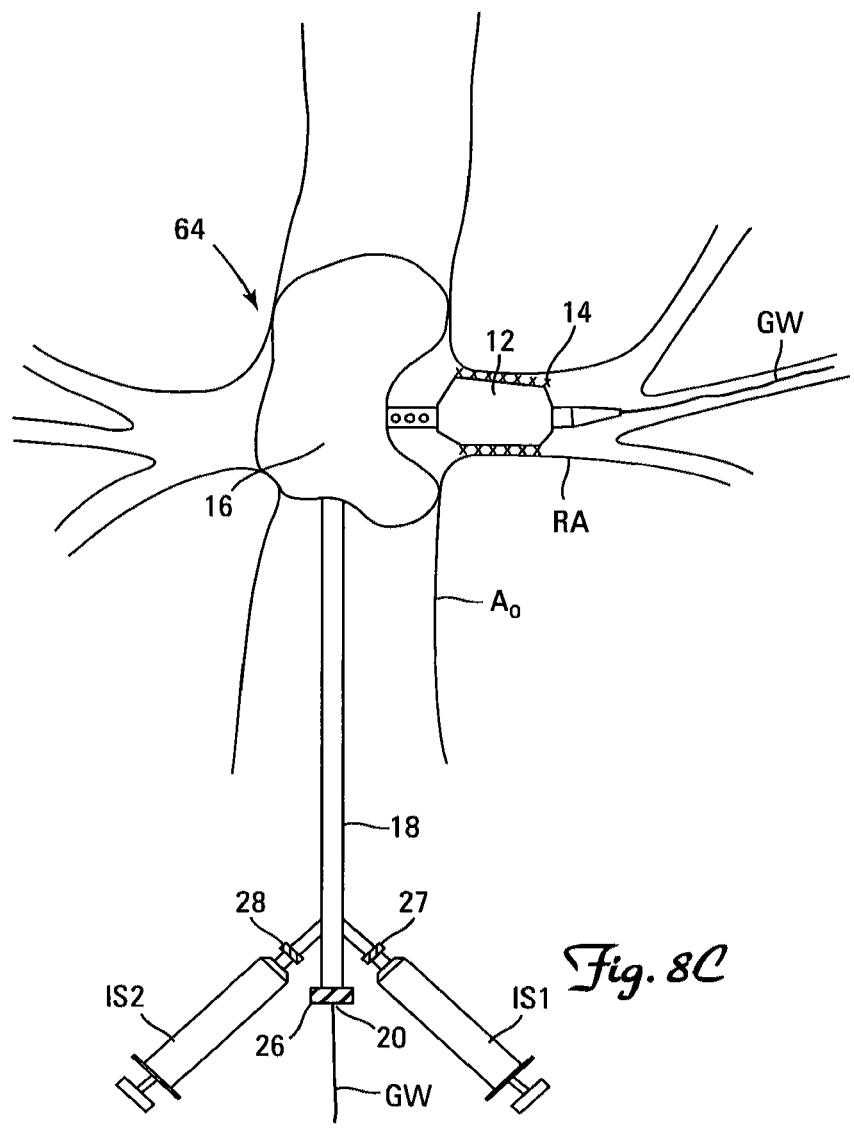
Figure 8D:
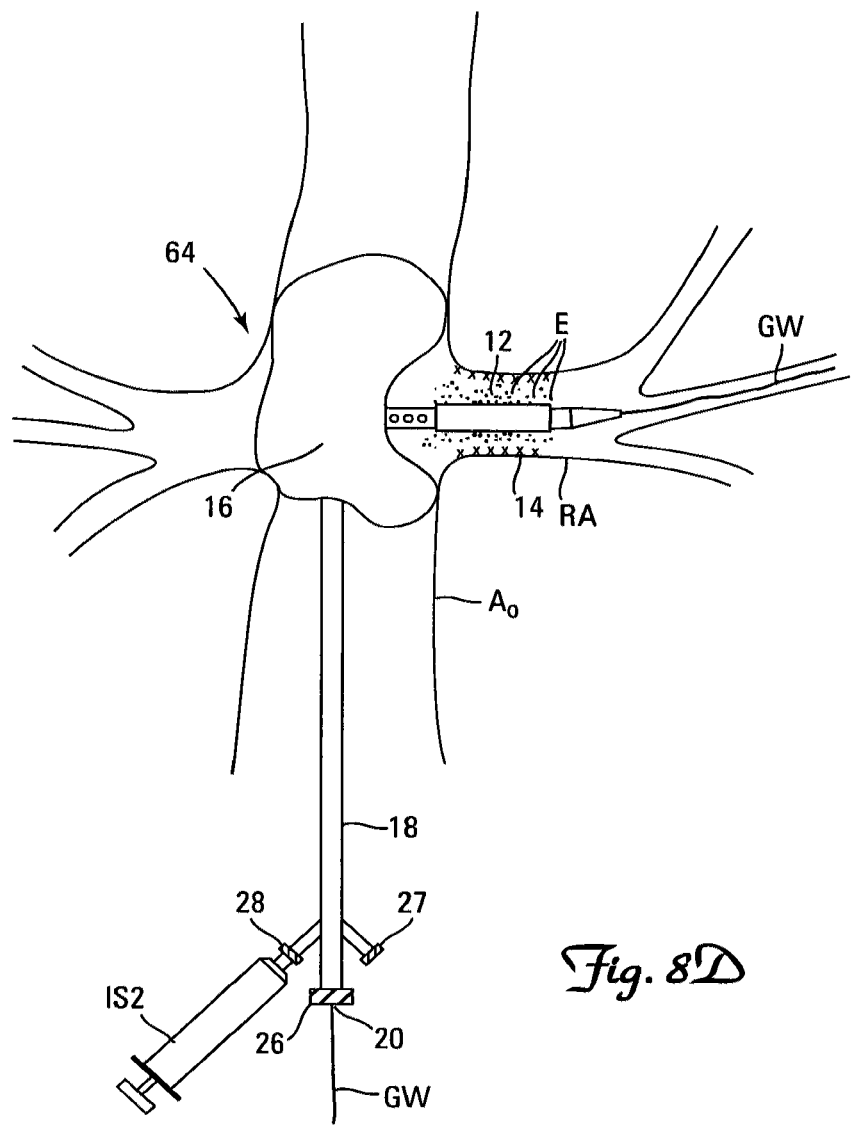

As illustrated in FIG. 8C, occlusion balloon 16 is inflated to occlude aorta Ao and prevent flow from aorta into renal artery RA. Inflation source IS2, for example a syringe or a high pressure inflation device, is attached to occlusion balloon hub 28 and occlusion balloon 16 is inflated using inflation source IS2. Following inflation of occlusion balloon 16 dilation balloon 12 is deflated using inflation device IS1. Inflation device IS1 may be removed from dilation balloon hub 27 as illustrated in FIG. 8D. Emboli E, created during dilation of lesion L, remain in the vicinity of deflated dilation balloon 12 because there is no flow in renal artery RA due to occlusion of aorta Ao caused by dilated occlusion balloon 16.

Figure 8E:
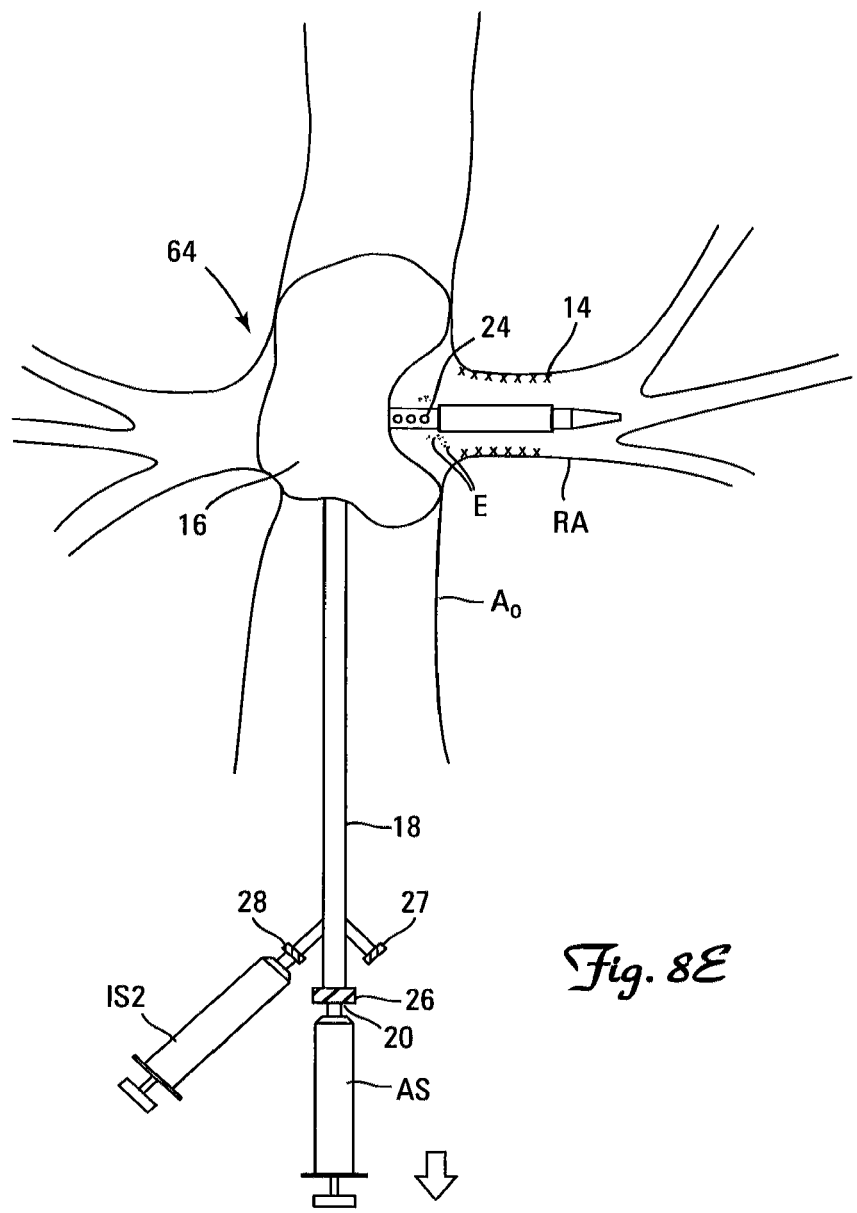

As illustrated in FIG. 8E, guidewire GW is removed from system 64 and aspiration device AS, for example a syringe, preferably as large as or larger than 30 cc capacity, is attached to aspiration hub 26. A vacuum is then drawn in aspiration device AS and emboli E are drawn from vicinity of stent 14 into aspiration holes 24 and proximally through lumen 20 into aspiration device AS. Alternatively, guidewire GW can be threaded through distal hub 42 and hemostasis valve 46 of adaptor 40 and aspiration hub 26 connected to distal hub 42. Hemostasis valve 46 is tightened to seal around guidewire GW and aspiration device AS is attached to sidearm hub 44. A vacuum is then drawn in aspiration device AS and emboli E are drawn from vicinity of stent 14 into aspiration holes 24 and proximally through lumen 20 into aspiration device AS.

Figure 8F:
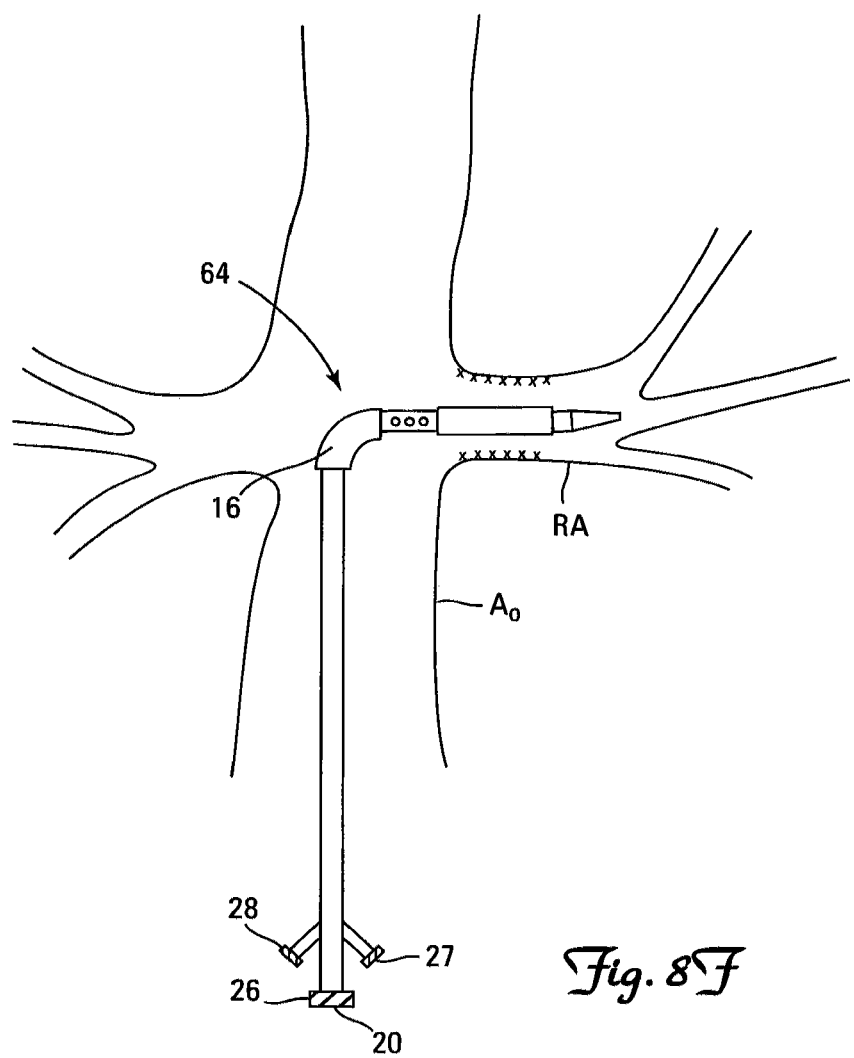

After aspiration of emboli E from renal artery RA in vicinity of stent 14 aspiration device AS can be removed from aspiration hub 26, occlusion balloon 16 is deflated, and inflation device IS2 is removed from occlusion balloon hub 28 as shown in FIG. 8F. Embolic protection and stent delivery system 64 can then be removed from the body.

An illustrative method of using embolic protection and stent delivery system 70 is substantially the same as the method shown in FIGS. 8A to 8F and described above. However, the manner of stent deployment for embolic protection and stent delivery system 70 differs from that described for embolic protection and stent delivery system 10. Rather than inflating dilation balloon 12 to compress lesion L and expand stent 14, as illustrated in FIG. 8B, stent 74 of embolic protection and stent delivery system 70 is deployed by withdrawing sheath 72 proximally relative to self-expanding stent 74 thereby allowing stent 74 to self-expand into contact with lesion L. It is important to withdraw distal end 76 of sheath 72 proximal of occlusion balloon 16 so that occlusion balloon 16 can expand and occlude the aorta Ao, as described in conjunction with FIG. 8C. Aside from details regarding how the stent is expanded the method of use of embolic protection and stent delivery system 70 is substantially the same as that described for embolic protection and stent delivery system 10.

FIG. 9 illustrates conceptually a partial cross-sectional diagram of an alternate embodiment of an embolic protection and stent delivery system in accordance with the present invention. Embolic protection and stent delivery system 90 is similar in most respects to embolic protection and stent delivery system 10 except that a perfusion lumen 92 having lumenal wall 94 has been added to occlusion balloon 98. In use aortic blood will flow through perfusion lumen 92 thereby preserving blood flow to the legs during the procedure. Flow into renal artery RA will be prevented when occlusion balloon 98 is inflated. Advantageously, occlusion balloon 98 is shaped to provide a pocket 95 in the vicinity of the juncture of renal artery RA and aorta Ao so that stent 14 can extend slightly into the aorta, a common clinical practice.

While this document has described an invention mainly in relation to renal artery stenting and embolic protection, it is envisioned that the invention can be applied to other conduits in the body as well including arteries, veins, bronchi, ducts, ureters, urethra, and other lumens intended for the passage of air, fluids, or solids. The invention can be applied to any site of branching of an artery, vein, bronchus, duct, ureter, urethra, and other lumen including but not limited to the junction of the common, internal, and external carotid arteries, the junction of the main, left anterior descending, and circumflex coronary arteries, the junction of the left main or right coronary artery with the aorta, the junction of the aorta with the subclavian artery, and the junction of the aorta with the carotid artery.

While the various embodiments of the present invention have related to stents and stent delivery systems, the scope of the present invention is not so limited. For example, it is understood that the invention does not require a stent or deployment of a stent, rather the invention can be used for a balloon angioplasty procedure without stenting. Further, while choices for materials and configurations may have been described above with respect to certain embodiments, one of ordinary skill in the art will understand that the materials described and configurations are applicable across the embodiments.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents.

What is claimed is:

1. A method for deploying a stent within a patient's blood vessel, the method comprising:
   providing an apparatus for removing emboli from a vessel during an interventional procedure, the apparatus comprising a single catheter, a self-expanding stent, and a sheath, the single catheter comprising:
   a single catheter shaft configured to be advanced along the patient's blood vessel, the single catheter shaft having a proximal portion, a distal portion, a proximal end, a distal end, and a lumen extending from the proximal end to the distal end;
   an occlusion element directly connected to and located on a distal portion of the single catheter shaft, the occlusion element having a contracted state and an expanded state;
   one or more aspiration ports located on a distal portion of the single catheter shaft, and one or more of the aspiration ports being located distal of the occlusion element; and
   a dilation element directly connected to and located on a distal portion of the single catheter shaft, the dilation element having a contracted state and an expanded state, and the dilation element being located distal of the occlusion element;
   the stent being disposed on the catheter distal of the occlusion element, and the sheath being disposed over the stent and the occlusion element;

advancing the catheter to a target site within the patient's blood vessel;

moving the sheath proximally relative to the stent so that the sheath is no longer disposed over the stent or the occlusion element and allowing the stent to self-expand;

expanding the occlusion element;

expanding the dilation element;

while the occlusion element is expanded, contracting the dilation element and then aspirating blood through the one or more aspiration ports; and after the blood has been aspirated, contracting the occlusion element.

2. The method of claim 1, wherein the dilation element is distal of the one or more aspiration ports.

3. The method of claim 1, wherein the stent is disposed over the dilation element when the sheath is disposed over the stent and the occlusion element.

4. The method of claim 1, wherein the dilation element is expanded, and then the occlusion element is expanded.

5. The method of claim 1, wherein the occlusion element comprises a balloon.

6. The method of claim 1, wherein the dilation element comprises a balloon.

7. The method of claim 6, wherein the occlusion element comprises a balloon.

8. The method of claim 5, wherein the catheter comprises an occlusion balloon hub on the proximal portion of the catheter and an occlusion balloon lumen connecting the occlusion balloon hub and the occlusion element.

9. The method of claim 6, wherein the catheter comprises a dilation balloon hub on the proximal portion of the catheter and a dilation balloon lumen connecting the dilation balloon hub and the dilation element.

10. The method of claim 1, wherein the distal portion of the catheter is positioned in a renal artery of the patient.

11. The method of claim 10, wherein the occlusion element is positioned in the renal aorta and the dilation element is positioned in the renal artery.

12. The method of claim 1, wherein the single catheter shaft comprises a sidewall around the lumen and the one or more aspiration ports are holes through the sidewall.

13. The method of claim 1, wherein the catheter comprises two or more aspiration ports.

14. The method of claim 13, wherein the single catheter shaft comprises a sidewall around the lumen and the two or more aspiration ports are holes through the sidewall.

15. The method of claim 1, wherein the catheter comprises a skive.

16. The method of claim 15, wherein the skive is located on a distal portion of the single catheter shaft, proximal of the occlusion element.

17. The method of claim 15, wherein the skive is located on a distal portion of the single catheter shaft, distal of the occlusion element.

18. The method of claim 1, wherein the catheter has a pre-set bend.

19. The method of claim 18, wherein the pre-set bend is at an angle of from about 10 degrees to about 170 degrees.

20. The method of claim 18, wherein the pre-set bend is at an angle of from about 45 degrees to about 135 degrees.

21. The method of claim 18, wherein the pre-set bend is at an angle of from about 75 degrees to about 105 degrees.

22. The method of claim 18, wherein the pre-set bend is at an angle of about 90 degrees.

23. The method of claim 18, wherein the pre-set bend is located proximal of the occlusion element.

24. The method of claim 18, wherein the pre-set bend is located at the occlusion element.

25. The method of claim 18, wherein the pre-set bend is located distal of the occlusion element.

26. The method of claim 1, wherein the occlusion element comprises a perfusion lumen.

27. The method of claim 1, wherein the occlusion element has a longitudinal axis and the perfusion lumen encompasses the longitudinal axis.

28. The method of claim 1, wherein the catheter is advanced to the target site over a guidewire.

* * * * *